United States Patent [19]

Baasner et al.

[11] 4,351,974
[45] Sep. 28, 1982

[54] PREPARATION OF 3-BROMO-4-FLUOROTOLUENE

[75] Inventors: Bernd Baasner; Erich Klauke; Ernst Kysela, all of Leverkusen, Fed. Rep. of Germany

[73] Assignee: Bayer Aktiengesellschaft, Leverkusen, Fed. Rep. of Germany

[21] Appl. No.: 233,413

[22] Filed: Feb. 11, 1981

[30] Foreign Application Priority Data

Mar. 4, 1980 [DE] Fed. Rep. of Germany ....... 3008158

[51] Int. Cl.$^3$ .............................................. C07C 25/13
[52] U.S. Cl. .................................................. 570/174
[58] Field of Search ......................................... 570/174

[56] References Cited

U.S. PATENT DOCUMENTS 3,591,645 7/1971 Selwitz ............................... 570/208

FOREIGN PATENT DOCUMENTS 1668163 9/1970 Fed. Rep. of Germany .
1923656 9/1970 Fed. Rep. of Germany .

OTHER PUBLICATIONS

Chem. Abst., vol. 62, 7662f (1965), Jargillo.
Chem. Abst., vol. 64, 9649c (1966) Merhar et al.
Chem. Abst., vol. 80, 132, 990j, 132992m, 132993n (1974), Komiyama et al.
Chem. Abst., vol. 81, 25308s (1974) Komiyama.

*Primary Examiner*—Thomas A. Waltz
*Assistant Examiner*—A. Pal
*Attorney, Agent, or Firm*—Sprung, Horn, Kramer & Woods

[57] ABSTRACT

In the preparation of 3-bromo-4-fluorotoluene by reacting 4-fluorotoluene with bromine, the improvement which comprises effecting the bromination in glacial acetic acid in the presence of iodine and iron or an iron salt. As a result the proportion of 3-bromo-4-fluorotoluene relative to its 2-bromo-4-fluorotoluene isomer is markedly increased.

5 Claims, No Drawings

PREPARATION OF 3-BROMO-4-FLUOROTOLUENE

The present invention relates to an unobvious process for the preparation of 3-bromo-4-fluorotoluene by bromination of 4-fluorotoluene.

It was known that a mixture of the isomers 3-bromo-4-fluorotoluene and 2-bromo-4-fluorotoluene is obtained by bromination of 4-fluorotoluene in carbon tetrachloride with iron as a catalyst (see J. Ind. Chem. Soc. 21, 112 (1944)) or by bromination of 4-fluorotoluene in undiluted form with aluminum tribromide as a catalyst (see Recl. Trav. Chim. Pays-Bas 82, 965 (1963)). When these processes were repeated, it was found that the ratio of the isomers relative to one another is about 20:80. Moreover, up to 10% of dibromo-4-fluorotoluene are obtained. The disadvantage of these reaction procedures is therefore the adverse proportion of the 3-bromo-4-fluorotoluene isomer of about 20%.

The present invention provides a process for the preparation of 3-bromo-4-fluorotoluene by the bromination of 4-fluorotoluene characterized in that the bromination is carried out in glacial acetic acid as the solvent, and in the presence of iodine and iron or an iron salt.

In this reaction, 3-bromo-4-fluorotoluene is obtained in a significantly higher yield than in prior art processes, that is to say in a proportion of up to 70%, compared with 30% of 2-bromo-4-fluorotoluene. This isomer ratio is achieved only when the catalyst system according to the invention is used.

The course of the reaction in the process is represented by the following equation:

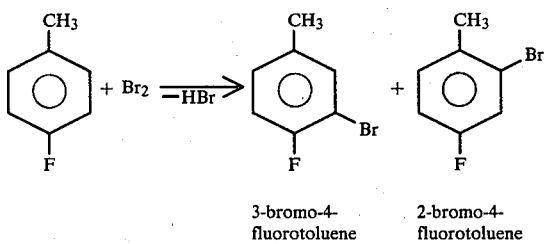

3-bromo-4-fluorotoluene    2-bromo-4-fluorotoluene

In carrying out the process according to the invention, generally 0.01 to 10 percent by weight of iron powder or iron salts and 0.01 to 10 percent by weight of iodine, in each case relative to the weight of 4-fluorotoluene employed, are added to an about 30 to 90% strength, preferably about 70 to 75% strength, solution of 4-fluorotoluene in glacial acetic acid. It is advantageous to prepare the iron powder by reduction.

It is most advantageous to use about 0.05 to 0.15 percent by weight of iron powder or iron salts and about 0.05 to 0.15 percent by weight of iodine, relative to the 4-fluorotoluene.

A 30 to 95% strength, preferably a 70 to 75% strength, solution of bromine in glacial acetic acid is preferably added, at about $-10°$ C. to $+50°$ C., preferably about $+20°$ C. to $+30°$ C., to a mixture prepared in the above manner. The molar ratio of 4-fluorotoluene to bromine should be about 1:0.8 to 1:1.5, preferably about 1:1 to 1:1.1 but most advantageously about 1:1. The reaction mixture is then subsequently stirred at temperatures between about $+20°$ C. and $+35°$ C. under normal pressure for about 3 to 18 hours. If the batch has a very large volume, it is advantageous to extend this subsequent reaction time.

The most favorable procedure for the process according to the invention consists in adding the solution of bromine in glacial acetic acid to the mixture of glacial acetic acid, 4-fluorotoluene and catalysts all at once, that is to say, the addition of bromine to the rest of the reaction mixture is effected as rapidly as possible, since the formation of dibromo-4-fluorotoluenes thus remains restricted to at most 2%. Moreover, a subsequent stirring time of 3 to 8 hours is already sufficient to obtain a relevant conversion of 4-fluorotoluene.

The reaction mixture is worked up by distillation. The crude mixture can be fractionated directly from the reaction vessel, under normal pressure or reduced pressure. However, it is most advantageous for the entire distillable content first to be distilled off, in vacuo, from a small amount of residue, which is predominantly composed of more highly brominated toluenes. Side reactions and decomposition reactions can thus largely be prevented by avoiding severe exposure of the crude mixture to heat. The crude distillate is then separated by distillation on a column, under normal pressure or reduced pressure. The first fraction, which consists of solvent and unreacted 4-fluorotoluene, can be employed again in bromination reactions on 4-fluorotoluene.

At a 4-fluorotoluene conversion of, for example, 40%, an isomer ratio of 3-bromo-4-fluorotoluene to 2-bromo-4-fluorotoluene of (60 to 70) % to (40 to 30) % is obtained. An increase in the conversion is achieved simply by extending the reaction time, the isomer ratio remaining unchanged.

PREPARATIVE EXAMPLES

Example A (Process known from the literature, according to J. Ind. Chem. Soc. 21, 112 (1944))

11 g of iron powder were added to a solution of 110 g (1 mole) of 4-fluorotoluene in 165 ml of carbon tetrachloride. 160 g (1 mole) of bromine were added dropwise to this mixture at room temperature, the mixture was subsequently stirred for 24 hours, the solvent was distilled off under normal pressure and the residue was fractionated under normal pressure over a 10 cm Vigreux column. 26.4 g of unreacted 4-fluorotoluene were obtained as the first fraction at a boiling point of 114° to 117° C., and 78 g of a mixture consisting of 66% of 2-bromo-4-fluorotoluene, 24% of 3-bromo-4-fluorotoluene and 9% of dibromo-4-fluorotoluene were obtained as the second fraction at a boiling point of 175° to 185° C. Relative to the 4-fluorotoluene reacted, the yield of 2-bromo-4-fluorotoluene plus 3-bromo-4-fluorotoluene was 48% and that of 3-bromo-4-fluorotoluene was 11.4%.

Example B (Process known from the literature, according to Recl. Trav. Chim. Pays-Bas 82, 965 (1963))

2.67 g of aluminum tribromide and 16.0 g of bromine were added to 110 g of 4-fluorotoluene, which had been cooled to $-15°$ C. After increasing the temperature to $+10°$ C., hydrolysis was carried out with water, the mixture was extracted by shaking with methylene chloride and the methylene chloride phase was washed and dried. After distilling off the solvent and the excess 4-fluorotoluene, 5.5 g of a mixture consisting of 88% of 2-bromo-4-fluorotoluene, 8% of 3-bromo-4-fluorotoluene and 4% of dibromo-4-fluorotoluene were obtained at a boiling point of 172° to 184° C. (normal pressure). Relative to the 4-fluorotoluene reacted, the yield of 3-bromo-4-fluorotoluene was 2.3%.

EXAMPLE 1

A solution of 160 g of bromine in 60 ml of glacial acetic acid was added, in the course of 3 hours, to a solution of 110 g of 4-fluorotoluene in 40 ml of glacial acetic acid, to which 1.1 g of iron powder and 1.1 g of iodine had been added. The initially exothermic reaction was kept at 25° C. to 27° C., first by cooling with water and then with warm water. The mixture was subsequently stirred at the above temperature for 8 hours, the glacial acetic acid and unreacted 4-fluorotoluene were then distilled off under normal pressure up to a temperature of 120° C. and a mixture consisting of 3-bromo-4-fluorotoluene (62%), 2-bromo-4-fluorotoluene (32%) and dibromo-4-fluorotoluene (5%) was subsequently distilled off under 20 mbars and between 65° C. and 85° C. 34 g of residue remained. The monobrominated isomers were separated by distillation on a column. 12.7 g of 2-bromo-4-fluorotoluene (boiling point: 176°–8° C. (normal pressure), $n_D^{20}$: 1.5260) and 24.5 g of 3-bromo-4-fluorotoluene (boiling point: 184°–5° C., (normal pressure), $n_D^{20}$: 1.5303) were obtained.

EXAMPLE 2

A solution of 160 g of bromine in 60 ml of glacial acetic acid was added all at once to a solution of 110 g of 4-fluorotoluene in 40 ml of glacial acetic acid, to which 1.1 g of iron powder and 1.1 g of iodine had been added. The initially exothermic reaction was kept at 25° C. to 27° C., first by cooling with water and then with warm water. The mixture was subsequently stirred at the above temperature for 3 hours, the glacial acetic acid and unreacted 4-fluorotoluene were then distilled off in vacuo and a mixture consisting of 3-bromo-4-fluorotoluene (57%), 2-bromo-4-fluorotoluene (41.9%) and dibromo-4-fluorotoluene (1.1%) was subsequently distilled off under 20 mbars and between 65° C. and 85° C. 8 g of residue remained. The monobrominated isomers were separated by distillation on a column. 21.5 g of 2-bromo-4-fluorotoluene (boiling point: 176°–8° C. (normal pressure)) and 28.5 g of 3-bromo-4-fluorotoluene (boiling point 184°–5° C. (normal pressure)) were obtained.

The isomer distributions obtained by the various processes are summarized in the following table:

| Process according to Example | Proportion (%) of | | |
|---|---|---|---|
| | 2-bromo-4-fluorotoluene | 3-bromo-4-fluorotoluene | dibromo-4-fluorotoluene |
| A | 66 | 24 | 9 |
| B | 88 | 8 | 4 |
| 1 | 32 | 62 | 5 |
| 2 | 41.9 | 57 | 1.1 |

It will be understood that the specification and examples are illustrative but not limitative of the present invention and that other embodiments within the spirit and scope of the invention will suggest themselves to those skilled in the art.

What is claimed is:

1. In the preparation of 3-bromo-4-fluorotoluene by reacting 4-fluorotoluene with bromine, the improvement which comprises effecting the bromination in glacial acetic acid in the presence of iodine and iron or an iron salt.

2. A process according to claim 1, wherein about 0.01 to 10 percent by weight of iron powder or an iron salt and about 0.01 to 10 percent by weight of iodine, in each case relative to the weight of 4-fluorotoluene employed, are added to an approximately 70 to 75% solution of 4-fluorotoluene in glacial acetic acid.

3. A process according to claim 2, wherein about 0.05 to 0.15 percent by weight of iron powder or an iron salt and about 0.05 to 0.15 percent by weight of iodine, relative to the 4-fluorotoluene, are employed.

4. A process according to claim 1, wherein the molar ratio of 4-fluorotoluene to bromine is from about 1:1 to 1:1.1.

5. A process according to claim 4, wherein about 0.5 to 0.15 percent by weight of iron powder or an iron salt and about 0.05 to 0.15 percent by weight of iodine, in each case relative to the weight of 4-fluorotoluene employed, are added to an approximately 70 to 75% solution of 4-fluorotoluene in glacial acetic acid.

* * * * *